(12) United States Patent
Garitano et al.

(10) Patent No.: US 6,689,095 B1
(45) Date of Patent: Feb. 10, 2004

(54) NEEDLELESS PERMANENT MAKEUP AND TATTOO DEVICE

(76) Inventors: Gilbert Garitano, 943 Pacific Ave., Alameda, CA (US) 94501; Linda Garitano, 943 Pacific Ave., Alameda, CA (US) 94501

( * ) Notice: Subject to any disclaimer, the term of this patent is extended or adjusted under 35 U.S.C. 154(b) by 0 days.

(21) Appl. No.: 09/556,081

(22) Filed: Apr. 21, 2000

Related U.S. Application Data

(60) Provisional application No. 60/130,737, filed on Apr. 22, 1999.

(51) Int. Cl.$^7$ .................................. A61M 5/30
(52) U.S. Cl. ........................ 604/70; 606/186
(58) Field of Search ................. 81/9.22; 128/919; 604/68–72, 181–183, 186–187, 207, 214, 218; 606/185–186, 116, 117

(56) References Cited

U.S. PATENT DOCUMENTS

| | | | |
|---|---|---|---|
| 2,754,818 A | 7/1956 | Scherer | 128/173 |
| 2,840,076 A | 6/1958 | Robbins | 128/253 |
| 3,115,133 A | 12/1963 | Morando | 128/173 |
| 3,688,765 A | 9/1972 | Gasaway | 128/173 |
| 4,089,334 A * | 5/1978 | Schwebel et al. | |
| 4,421,508 A | 12/1983 | Cohen | 604/70 |
| 4,508,106 A | 4/1985 | Angres | 128/316 |
| 4,596,556 A | 6/1986 | Morrow et al. | 604/70 |
| 4,623,332 A | 11/1986 | Lindmayer et al. | 604/68 |
| 4,643,721 A | 2/1987 | Brunet | 604/191 |
| 4,644,952 A | 2/1987 | Patipa et al. | 606/167 |
| 4,670,223 A | 6/1987 | Delachapelle | 422/4 |
| 4,790,824 A | 12/1988 | Morrow et al. | 604/143 |
| 4,798,582 A * | 1/1989 | Sarath et al. | |
| 5,062,830 A | 11/1991 | Dunlap | 604/68 |
| 5,064,413 A | 11/1991 | McKinnon et al. | 604/70 |
| 5,176,642 A | 1/1993 | Clement | 604/135 |
| 5,230,727 A | 7/1993 | Pound et al. | 55/492 |
| 5,480,381 A | 1/1996 | Weston | 604/68 |
| 5,503,627 A | 4/1996 | McKinnon et al. | 604/72 |
| 5,520,639 A | 5/1996 | Peterson et al. | 604/68 |
| 5,550,187 A * | 8/1996 | Rhee et al. | 424/423 |
| 5,569,189 A | 10/1996 | Parsons | 604/68 |
| 5,593,388 A | 1/1997 | Phillips | 604/134 |
| 5,599,302 A * | 2/1997 | Lilley et al. | |
| 5,643,211 A | 7/1997 | Sadowski et al. | 604/110 |
| 5,649,912 A | 7/1997 | Peterson | 604/187 |
| 5,697,917 A | 12/1997 | Sadowski et al. | 604/218 |
| 5,704,911 A | 1/1998 | Parsons | 604/72 |
| 5,722,953 A | 3/1998 | Schiff et al. | 604/68 |
| 5,769,138 A | 6/1998 | Sadowski et al. | 141/329 |
| 5,782,802 A | 7/1998 | Landau | 604/68 |
| 5,795,371 A | 8/1998 | Ezio et al. | 96/175 |
| 5,851,198 A | 12/1998 | Castellano et al. | 604/68 |
| 5,893,397 A | 4/1999 | Peterson et al. | 141/27 |
| 5,993,412 A | 11/1999 | Deily et al. | |
| 6,033,421 A | 3/2000 | Theiss et al. | 606/185 |

* cited by examiner

*Primary Examiner*—LoAn H. Thanh
(74) *Attorney, Agent, or Firm*—Medlen & Carroll, LLP

(57) ABSTRACT

The present invention relates to methods and compositions for the needleless administration of permanent makeup and tattoos. In particular, the present invention relates to hypodermic injectors for use in delivering pigment or other desired substances to targeted layers of the skin, avoiding needlestick injuries and transmission of disease to the treated subject.

1 Claim, 2 Drawing Sheets

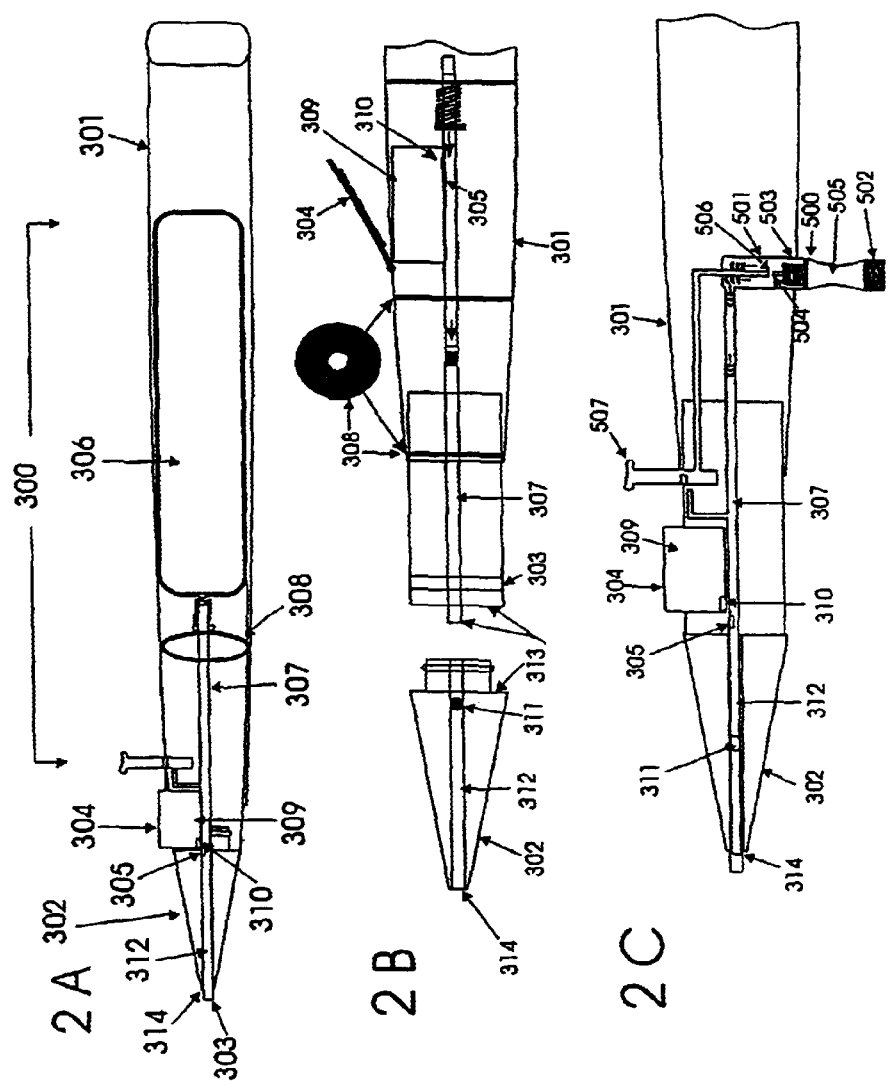

NEEDLELESS PERMANENT MAKEUP AND TATTOO DEVICE

This application claims the benefit of Provisional Application Ser. No. 60/130,737 filed Apr. 22, 1999.

FIELD OF THE INVENTION

The present invention relates to methods and compositions for the needleless administration of permanent cosmetics and tattoos. In particular, the present invention relates to hypodermic injectors for use in delivering pigment or other desired materials to targeted layers of the skin.

BACKGROUND OF THE INVENTION

Since ancient times, people have used paint and other coloring techniques to improve attractiveness and for cultural or religious purposes. Today, many people seek permanent colorations or other permanent or long-term cosmetic enhancement as a substitute for repeated application of cosmetics. A number of intradermal injection and surgical devices for use in applying permanent cosmetics have been known for years. They are commonly used, for example, to create decorative tattoos on a person's skin or to form permanent eyelid liners to replace paint-on cosmetic eyelid liners. The devices inject ink, dye, or other marking fluid just under the skin surface, so that the ink is retained within the skin and the color of the ink and the design formed by the ink injection pattern is visible.

The devices use a skin-penetrating needle which has the capacity to retain some quantity of ink or dye, a mechanism to reciprocate the needle for repeated punctures of the skin to implant the ink under the skin in the desired pattern, and a pen-like housing which the operator holds and uses to guide the device. A number of different devices, particularly with different types of reciprocating needle drives, have been disclosed over the years (See e.g., U.S. Pat. Nos. 2,840,076; 4,508,106; 4,644,952; 4,798,582; and 6,033,421 herein incorporated by reference in their entireties).

All of the currently used methods for delivering permanent makeup, tattoo pigment, and other cosmetic materials to the subdermal tissue require the use of one or more needles that penetrate the skin to deliver the pigment or dye. The colored pigment is applied to the skin by superficially puncturing the skin, and moving the needle in an axial reciprocal motion in and out of the skin to urge the color pigment into position just under the skin, where the pigment is permanently retained. This procedure inevitably involves exposure of the needle to blood in the body tissues. Such methods present a risk of disease transmission and infection, pain, and apprehension in treated subjects.

Because of the HIV and hepatitis epidemics, among a host of other diseases, healthcare and other professionals who routinely use needles have raised serious concerns about their health and safety, as well as that of their subjects. For example, the once routine procedure of administering cosmetics through the use of needles may be a life-threatening event. Infectious diseases have been transmitted to healthcare workers and other professionals by needlestick and sharp injuries. For example, over one million needlestick injuries are reported every year. Sixty to ninety percent of all reported needlestick injuries are incurred by the administering personnel. Indeed, needlestick injuries are the most common occupational injury experienced by healthcare professionals. Needlestick injuries have been shown to transmit a large number of infectious diseases, including, AIDS, blastomycosis, brucellosis, cyptococosis, diphtheria, Ebola fever, gonorrhea (cutaneous), hepatitis B, herpes, hepatitis C, malaria, leptospirosis, mycobacteriosis, Rocky Mountain spotted fever, mycoplasmosis, staphylococcal infections, scrub typhus, toxoplasmosis, sporotrichosis, syphilis, streptococcal infections, and tuberculosis. Thus, the art is in need of methods and compositions for applying permanent cosmetics without the health risks, pain, and fear associated with conventional techniques.

SUMMARY OF THE INVENTION

The present invention relates to methods and compositions for the needleless administration of permanent makeup and tattoos. In particular, the present invention relates to hypodermic injectors for use in delivering pigment or other desired substances to targeted layers of the skin.

The present invention provides a system comprising a needleless injector suitable for injecting cosmetic material through a skin surface of a subject, the needleless injector comprising: a housing, wherein the housing includes an injection end comprising an orifice; an ampule containing the cosmetic material; a driver capable of forcing the cosmetic material out of the orifice of the injection end of the housing at a sufficient velocity to pierce the skin surface of the subject; and an energy mechanism for moving the driver. In some embodiments of the present invention, the cosmetic material comprises pigment. In other embodiments, the cosmetic material is selected from the group including, but not limited to, collagen, elastin, polypeptides, and nutrients.

The needleless injector of the present invention may be associated with a variety of features that improve safety and/or utility. For example, in some embodiments of the present invention, the needleless injector further comprises a nozzle tip. In preferred embodiments, the nozzle tip is detachably connected to the injection end of the housing. In other preferred embodiments, the nozzle tip is transparent. In yet other preferred embodiments, the nozzle tip comprises a pressure sensitive activator, wherein the activator is capable of activating the energy mechanism, for example, when the end of the injector is pressed against the skin surface of the subject.

In other embodiments, of the present invention, the needleless injector further comprises a trigger, wherein the trigger is capable of activating the energy mechanism. Triggers include, but are not limited to, levers, buttons, switches, or other easy to manipulate activation means.

In yet other embodiments of the present invention, the needleless injector comprises a plurality of ampules containing the cosmetic material. The ampules may be included within the needleless injector or may be external to the injector, but attached by one or more injection tubes to the injector.

In some preferred embodiments of the present invention, the energy mechanism comprises compressed gas. The compressed gas can be supplied in one or more gas cartridges, by an air compressor attached to the housing through one or more tubes, or any other means of delivering forces air through or into the injection device. In alternate embodiments, the energy mechanism is selected from a group including, but not limited to, springs and pyrotechnic charges.

The present invention further provides a method of injecting cosmetic material through a skin surface of a subject, comprising: providing a needleless injector, wherein the injector comprises the cosmetic material and a means for forcing the cosmetic material out of the injector at a sufficient velocity to pierce the skin surface of the subject;

placing a surface of the injector in contact with the skin surface of the subject; and activating the means for forcing the cosmetic material out of the injector at a sufficient velocity to pierce the skin surface of the subject.

The present invention also provides a method of injecting cosmetic material through a skin surface of a subject, comprising: providing any of the systems described above; placing the needleless injector of the system in contact with the skin surface of the subject; and activating the energy mechanism.

DESCRIPTION OF THE FIGURES

FIGS. 2A–C show a perspective view of a pigment applicator device in a second embodiment of the present invention.

GENERAL DESCRIPTION OF THE INVENTION

Figure 1:
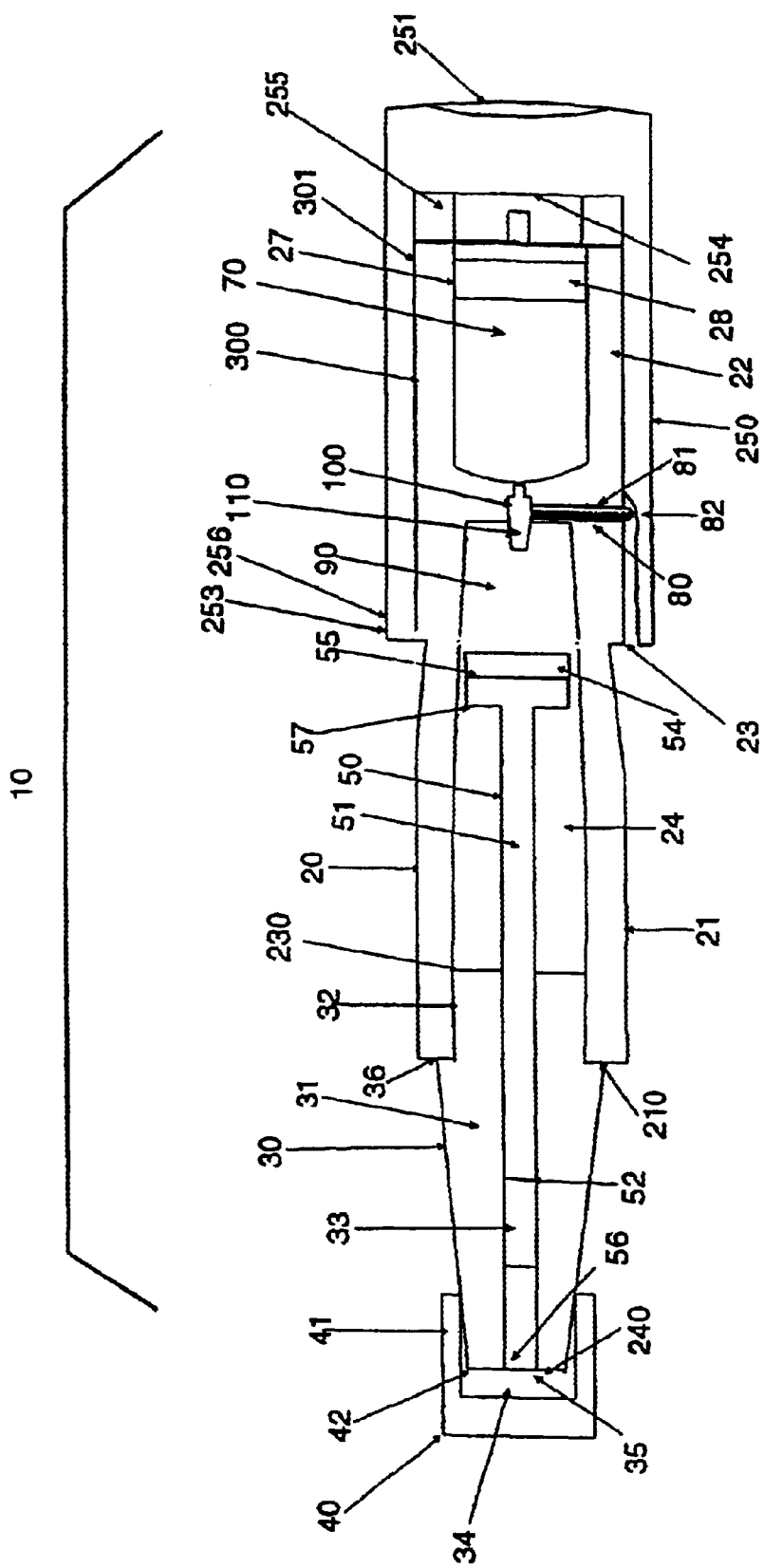
FIG. 1 shows a perspective view of a pigment applicator device in accordance with one embodiment of the present invention.

The present invention relates to methods and compositions for the needleless administration of permanent and semi-permanent makeup and tattoos. In particular, the present invention relates to hypodermic injectors for use in delivering pigment or other desired substances to targeted layers of the skin. The present invention provides devices that are safe, sterile, and needle-free, as well as methods that increase the comfort level of the application, eliminating the spread of blood borne-diseases and decreasing the apprehension level of subjects who obtain the treatment. The needleless injectors also afford a further advantage in that the injected material can be dispersed through a greater volume of tissue than when a bolus injection is introduced through a conventional hypodermic needle. Thus, the devices of the present invention provide dramatic new levels of safety and ease-of-use for permanent cosmetic applications, tattooing, and rehabilitation and repigmentation of surgical and burn patients (e.g., scar camouflage, breast cancer reconstruction, birth mark camouflage, burn camouflage, stretch mark camouflage, and the like). The devices also have the added advantage of reducing environmental contamination associated with needle disposal.

The devices of the present invention provide a needle-free micropigmentation delivery method, by, for example, epidermal air injection of micro-pigments, as well as dermatological substances such as collagen, elastin, polypeptides, and nutrients of various sorts, to the basal layers of the skin. As such, the methods do not involve the penetration of the skin by a needle, the devices prevent needlestick injuries and avoid the risk of exposure to blood-borne diseases, as well as lessening skin trauma and aiding in healing time as well as allowing a higher comfort level per procedure.

In some embodiments of the present invention, the devices use compressed air (e.g., a compressed inert gas such as carbon dioxide [$CO_2$]) as the power source to inject the micropigments or other substances through a microorifice, penetrating the epidermis within a fraction of a second. In other embodiments of the present invention, the devices use medical grade compressed ambient air supplied by a suitable air compressor. Methods and apparatuses capable of supplying medical grade pathogen free air suitable for use in the present invention are described in U.S. Pat. Nos. 5,795,371, 5,230,727, and 4,670,223, herein incorporated by reference in their entireties. The pigment deposition process of the present invention is repeated until the desired effect is achieved. The present invention is not limited to any particular power source, as a number of other delivery means provide a velocity sufficient to cause the injected material to pierce the skin and enter the underlying tissues. Such methods include, but are not limited to the use of springs, pyrotechnic charges or the like instead of gas power as the injection delivering force. Examples of power sources that find use with the present invention are found in hypodermic injectors used in the delivery of medication to the blood stream, including, for example, as described in U.S. Pat. Nos. 5,993,412; 5,593,388; 5,851,198; 5,769,138; 5,722,953; 5,704,911; 5,697,917; 5,643,211; 5,599,302; 5,569,189; 5,520,639; 5,503,627; 5,480,381; 5,176,642; 5,062,830; 5,064,413; 4,790,824; 4,643,721; 4,623,332; 4,596,556; 4,421,508; 4,089,334; 3,688,765; 3,115,133; 2,816,54; and 2,754,818, all of which are herein incorporated by reference in their entireties.

The size of the orifice through which the micro-pigment or dermatological substance is injected is determined by the size and the pressure contained within the gas cartridge or the pressure delivered by other energy sources, as well as the size and shape of the device nozzle tip that makes contact with the skin. These factors also affect the depth of penetration into the skin. As a result of this procedure, micropigment or other injected material is permanently deposited under the surface of the skin. The device can be adjusted to regulate the depth of the injection as desired, in order to allow deposit of the injected material to the appropriate depth for achieving, for example, permanent coloration (i.e., as opposed to temporary coloration).

In some embodiments, of the present invention, the needleless injector further comprises a liquid-transfer apparatus designed to facilitate the fluid transfer of the pigment or cosmetic material into the injection chamber prior to delivery to the target. (See e.g., U.S. Pat. No. 5,893,397, herein incorporated by reference in its entirety). In other embodiments of the present invention, the ampules are filled prior to using the needless injector by any of a number of ampule filing devices (See e.g., U.S. Pat. No. 5,649,912 herein incorporated by reference in its entirety).

In preferred embodiments of the present invention, sterile nozzle tips are the only part of the device that make direct contact with the skin, and may be disposed of after each procedure. The compressed air may be provided in a pressurized gas cartridge, wherein the sterile gas cartridges make no direct contact with the skin, and can also be disposed of after each use, eliminating any chance of contamination. The compressed air may also be provided through attachment of the device with a suitable air compressor or other source of pressurized air.

In some embodiments of the present invention, the device has a pressure sensitive deployment mechanism that ensures proper seating of the injector face against the skin surface before sample delivery is accomplished. A second level of safety can be employed by requiring both proper seating of the injector face and depression of an activation button or switch by the technician. Thus, the needleless injector device assures safe use, even by inexperienced operators under adverse conditions.

The present invention also provides methods for the removal of pigment (e.g., tattoos and permanent cosmetics) from a subject. For example, rather than injecting a pigment to the subdermal tissue layers, the devices of the present invention are used to inject a removal solution to the subdermal layers to remove or reduce pigmentations. Any solution capable or reducing or removing coloration finds use with the present invention. For example, in some embodiments of the present invention, trichloracetic acid is applied to a pigmented area. In other embodiments of the present invention, nitric acid is applied to a pigmented area. In yet other embodiments of the present invention, removal may be conducted by injecting a solution that solubilizes the pigment and removing the solution. Any type of removal is contemplated. In some embodiments solution removal comprises suction or drainage of the solution from the skin. In preferred embodiments the skin is treated to facilitate removal. For example, the skin may be treated with heat, chemicals, hormones, and the like to open pores. In other embodiments of the present invention, removal comprises injecting a solution that carries the pigment into the bloodstream.

In preferred embodiments, the needleless injector is for use with human beings. However, it is contemplated that the present invention will find use in veterinary applications, as well as for identification of animals (e.g., tattooing and branding).

Definitions

To facilitate an understanding of the present invention, a number of terms and phrases are defined below:

As used herein, the term "needleless injector" refers to a device capable of introducing a material through the skin of a subject without the use of a needle. Needleless injectors may include a needle, for example, to draw the injectable material into the device prior to injection, but carry out the injection process without piercing the skin of the subject with a needle.

As used herein, the term "ampule" refers to a container for storing one or more injectable materials. Ampules may contain a single chamber or multiple chambers and can be made of any desirable material for storing the injectable material.

As used herein, the term "cosmetic material" refers to any material that is to be injected substantially beneath the skin surface for cosmetic purposes (i.e., as opposed to injection in the bloodstream for medical purposes). Cosmetic materials include, but are not limited to pigments, collagens, elastins, polypeptides, carbohydrates, lipids, and nutrients (e.g., vitamins).

As used herein, the term "pigment" refers to a substance used as coloring. Pigments include liquid and dry coloring material, and include, but are not limited to, pigments used in tattooing and permanent makeup applications.

As used herein, the term "energy mechanism" or "power source" refers to a system for delivering a force to a driver or other device or material. Energy mechanisms include, but are not limited to compressed gas, pyrotechnic charges, springs, and the like.

As used herein, the term "driver" refers to a portion of a device that imparts or transmits motion, power, or forceful pressure to another device part or to a material. Drives include, but are not limited to, pistons, levers, articulators, and the like.

As used herein, the term "sufficient velocity to pierce the skin surface of a subject" refers to a velocity capable of delivering an injectable material beneath the skin surface of a subject. In preferred embodiments, the velocity delivers the injectable material to the subdermal tissue, while avoiding substantial delivery to the bloodstream. The velocity will vary depending on the location, thickness, and type of skin. For example, fluid materials can be delivered beneath the skin if accelerated at a velocity between about 800 feet per second and 1,200 feet per second, although lower or higher velocities may be appropriate for particular injectable materials or skin types. It should be noted that, in some embodiments of the present invention, the needleless injector of the present invention deposits pigments and compositions in skin tissues to a sufficient depth in order to ensure that a permanent marking remains retained by the tissue, and such that a clearly visible marking remains after the passing of time, but not so deep that the deposited pigments or compositions enter the subject's blood supply. Velocity of the devices may be controlled by a number of factors including, but not limited to, the amount of force applied to the injectable material or the diameter of the passage, nozzle, or tip through which the injectable material travels. In some embodiments of the present invention, changes to velocity may be made by adjusting the device accordingly (e.g., adjusting the tension of a spring, adjusting the force applied by a pressurized gas, and adjusting the diameter of the passage, nozzle, or tip, by substituting a separate component into the device or by turning an adjustment dial that physically alters the diameter of the passageway). One skilled in the art is capable of testing the appropriate velocity for particular applications by, for example, testing a variety of velocities on a test animal or tissue. For example, a tissue sample corresponding to a tissue to be treated is injected using the device of the present invention and the location of the pigment is identified (e.g., by dissection, microscopy, and the like). In some embodiments, the test tissue is part of a living animal and the maintenance of the coloring is monitored over time. The presence and amount of injectable material that enters the blood stream for a particular velocity and tissue type can be detected by obtaining a blood sample and detecting the presence of the injectable material (e.g., detecting the presence of a detectable marker injected with the injectable material). Adjustments may also be made by the practitioner during a treatment simply by visual observation of undesired results (e.g., penetration that is too shallow or too deep), with corrections being made accordingly.

As used herein, the terms "suitable air compressor" or "suitable compressed air," and equivalents, are used in their broadest sense to describe a compressed air source free of pathogens.

As used herein, the term "medical grade air" refers to a pathogen free air.

As used herein, the terms "material" and "materials" refer to, in their broadest sense, any composition of matter.

As used herein, the term "pathogen" refers to disease-causing organisms or infectious agents, microorganisms, or agents including, but not limited to, viruses, bacteria, parasites (including, but not limited to, organisms within the phyla Protozoa, Platyhelminthes, Aschelminthes, Acanthocephala, and Arthropoda), fungi, and prions.

As used herein, the term "peptide" refers to any substance composed of two or more amino acids.

As used herein, the term "carbohydrate" refers to a class of molecules including, but not limited to, sugars, starches, cellulose, chitin, glycogen, and similar structures. Further, carbohydrates can occur as components of glycolipids and glycoproteins.

As used herein, the term "lipid" refers to a variety of compounds that are characterized by their solubility in organic solvents. Such compounds include, but are not limited to, fats, waxes, steroids, sterols, glycolipids, glycosphingolipids (including gangliosides), phospholipids, terpenes, fat-soluble vitamins, prostaglandins, carotenes, and chlorophylls. As used herein, the phrase "lipid-based materials" refers to any material that contains lipids.

As used herein, the term "organic solvents" refers to any organic molecules capable of dissolving another substance.

Examples include, but are not limited to, chloroform, alcohols, phenols, and ethers.

As used herein, the term "sample" is used in its broadest sense. In one sense it is meant to include a specimen or culture; on the other hand, it is meant to include biological and environmental samples. Biological samples include blood products, such as plasma, serum and the like. Biological samples may be animal, including human, fluid, solid or tissue. Environmental samples include environmental material such as surface matter, soil, water, crystals and industrial samples. These examples are not to be construed as limiting the sample types applicable to the present invention.

DETAILED DESCRIPTION OF THE INVENTION

The following examples are provided in order to demonstrate and further illustrate certain preferred embodiments and aspects of the present invention and are not to be construed as limiting the scope thereof.

As shown in FIG. 1, a needleless injection device according to one embodiment of the present invention is embodied in a pen-sized device. The needleless injector device (10) according to an embodiment of the invention is useful for hypodermic injection of pigment or other cosmetic material without piercing the skin with a needle.

The preferred embodiment ensures precise delivery through an orifice with a diameter of approximately 0.0032' (i.e., approximately 0.08 mm). However, larger or smaller diameters may be used, so long as accurate penetration of the skin and delivery of the injectable material is maintained (e.g., different diameters to regulate velocity of the injectable material or fineness or coarseness of the applied mark). In this embodiment, the injected material is linearly accelerated via pneumatic propulsion. Safety is maintained and inadvertent activation of the injection device (10) is avoided via a pressure sensitive (e.g., resistance) triggering feature that allows for proper tensioning of the nozzle and orifice at the injection site prior to automatic deployment and/or through activation of a control switch by the user. For example, activation of the injector device (10) will not occur until the injector is properly positioned to provide the required resistance from the skin surface of the subject to allow for sufficient tension and pressure to be applied to a trigger of the injector device (10) to activate it to deliver the dosage of injectable material. Improper positioning resulting in insufficient resistance by the skin surface of the subject will prevent the injector device (10) from being inadvertently activated. For example, tight tolerances between a trigger cap and a housing will prevent the cap from sliding along the housing to trigger the device (10), if the device (10) is more than 10 degrees off of an axis perpendicular to the skin surface of the subject to be treated.

The injector device (10) has a main body (20), a chamber housing (30), a cap (40), a piston (50), an actuating member (250), and a first gas chamber (70). The main body (20) includes a first body portion (21) integrally connected to a second body portion (22). The main body (20) comprising the first body portion (21) and second body portion (22) may be a single unit in design and manufacturing. In a preferred embodiment of the device, the second body portion (22) has a slightly larger diameter than that of the first body portion (21). A flange (23) is formed due to a larger diameter of the second body portion (22). The first body portion (21) and the second body portion (22) each has an elongated cylindrical shape. However, in alternative embodiments, other shapes (e.g., rectangular, triangular, octagonal or the like) may be used. The main body (20) also has an elongated cavity (24) centrally disposed along the length of the first body portion (21) and partially along the length of the second body portion (22). The elongated cavity (24) forms an opening that is located on the end of the main body (20), located opposite the second body portion (22). In some embodiments, the elongated cavity (24) has a cylindrical shape with a substantially homogenous diameter. However, in alternative embodiments, other shapes such as rectangular, triangular or the like may be used. In other embodiments, the diameter of the elongated cavity (24) gradually tapers off as the elongated cavity (24) nears the second body portion (22). In such embodiments, the smaller diameter portion of the elongated cavity (24) limits the backward movement of the piston (50) and tends to increase the rate of acceleration when the jet injection device (10) is first activated.

The second body portion (22) includes a lever passageway (80) and the first gas chamber (70) for storing compressed inert gas (e.g. carbon dioxide). However, alternative embodiments may use other gases or a gas/liquid combination. The elongated cavity (24), containing a second gas chamber (90), and the first gas chamber (70) are coupled together to provide gaseous communication with each other through a passageway (100). The first gas chamber (70) of the second body portion (22) has an opening on the opposite end of the passageway (100), through which compressed gas is pre-filled into the first gas chamber (70). A retention groove (27), preferably ring-shaped, is formed around the inner diameter of the first gas chamber (70) near the end of the large opening in the first gas chamber. A chamber plug (28) is disposed within the opening of the first gas chamber (70) to seal in the compressed inert gas, once the gas has been loaded. The chamber plug (28) forms an air tight seal in the first gas chamber (70) by engaging the retention groove (27). The retention groove (27) also prevents the chamber plug (28) from detaching itself from the second body portion (22) due to the presence of compressed gas in the first gas chamber (70). The chamber plug (28) is configured and sized to firmly fit into the opening of the first gas chamber (70). In alternative embodiments, instead of the retention groove (27), the inner surface of the first gas chamber may be threaded so that the chamber plug (28), with corresponding outer threads, may be screwed into the first gas chamber (70). Alternatively, the first gas chamber (70) may be a sealed compartment in which compressed gas is injected through a valve or may comprise a replaceable gas containing cartridge. A seal may be obtained by using an adhesive or other suitable materials. The chamber plug (28) may be made of any suitable rigid materials, such as plastic, rubber, ceramic, metal, composites and the like. Although the main body (20) may be made of plastic by such process as an injection molding, other suitable materials, such as ceramic, glass, metal, composites or the like, may be used. In addition, the first body portion (21) and the second body portion (22) may be formed together as one injection mold or may be formed from separate portions coupled together by adhesives, welding, snap fits or the like.

Inside the elongated cavity (24), a release valve (110) is attached to the wall to block off and seal the passageway (100). In its normal position, the release valve (110) blocks the gas flow from the first gas chamber (70) into the elongated cavity (24). When the release valve (110) is displaced from its original position, the compressed gas from the first gas chamber (70) is released into the elongated cavity (24). More specifically, the compressed gas is released into a second gas chamber (90), which is a part of the elongated cavity (24). The release valve (110) is preferably sufficiently large to fully cover the opening in the passageway (100), thus preventing any gas leakage. The release valve (110) is preferably displaced by applying force on its side, but it should be attached firmly enough to withstand the pressure exerted by the compressed air in the first gas chamber (70) or a shock (e.g., due to inadvertent mishandling of the device by the user, such as dropping the device). In addition, the release valve (110) should resist being displaced until the injector device (10) is placed in contact with the skin of a subject and sufficient resistance is encountered to permit the injector device (10) to be activated by applying sufficient pressure to displace the release valve (110).

In some embodiments, a lever passageway (80) may be formed on the side wall of the main body (20) and extends from the outer to the inner surface of the second body portion (22) at a slightly slanted angle. However, other configurations may be used. The lever passageway (80) is adapted and configured to hold a lever (81) which protrudes through the lever passageway (80). In one preferred embodiment, the lever (81) is a cylindrical rod with a rounded end (82). The rounded end (82) protrudes out of the second body portion (22). The lever (81) has preferably the sufficiently same cross-section and diameter as the lever passageway (80) to firmly fit inside the passageway (80) to provide a sufficiently tight air and fluid seal so as to not hinder with the effective performance of the injection device (10). However, there may be some clearance between the lever (81) and the passageway (80) to bleed-out excess gas pressure over a time, once the injector device (10) has been used. In an alternative embodiment, there may be a plurality of levers (81) disposed through a plurality of lever passageways (80) to ensure the displacement of a release valve (110). For example, in some embodiments, the main body (20) may accommodate two levers positioned at a 90 degree angle to each other, so that the combined force of the levers ensure proper displacement of the release valve (110). In alternative embodiments, the lever (81) and the passageway (80) may be formed in a rectangular rod shape or any other suitable shapes. In still other embodiments, the lever (81) may be made of resilient plastic or other suitable materials.

The chamber housing (30) includes an elongated tubular body (31), a neck portion (32), and a liquid chamber (33) for holding, prior to injection, pigment or other injectable material. The chamber housing (30) has an orifice (34) at one end and has an opening configured to receive the piston (50) at the other end. The orifice (34) is centrally positioned on an injector face (35). The injector face (35) has a flat surface, except that the center region around the orifice (34) is slightly raised. The raised surface around the orifice (34) provides firm contact against a receiving surface, such as the skin surface of the subject to be treated. This helps to insure that the injector is properly positioned and will not be activated until sufficient pressure is applied to the injector device (10).

In particularly preferred embodiments, the outer diameter of the neck portion (32) is smaller than the outer diameter of the elongated tubular body (31), which forms a shoulder portion (36) where the two parts join together. The shoulder portion (36) rests on the surface of the opening formed by the elongated cavity (24) of the main body (20). However, the outer diameter of the neck portion (32) is substantially the same as the inner diameter of the elongated cavity (24) of the main body (20), so that the neck portion (32) firmly fits inside the elongated cavity (24). To firmly engage the neck portion (32) of the chamber housing (30) with the elongated cavity (24) of the main body, the middle section of the neck portion (32) may have a slightly larger outer diameter that fits into a groove formed inside the elongated cavity (24). Once coupled together, the chamber housing (30) cannot be released from the main body (20), unless extreme force is applied. In alternative embodiments, the raised outer diameter of the neck portion is configured such that threads are present on the outer diameter of the neck portion (32) and matching threads are formed inside the elongated cavity (24) to screw-in the chamber housing (30). This provides the advantage of allowing the user to assemble the device (10) when needed or just prior to giving an injection. This assembly option also allows the user to select a variety of different treatments while minimizing the number of complete injectors (10) that must be carried or stocked. It also facilitates manufacture of the device (10), since the injector (10) and the chamber housing (30) may be manufactured at different times. Further, the main body (20) and the chamber housing (30) may be attached and sealed together by any suitable method, such as adhesives, welding or the like. A ring joint (210), in the form of a plastic weld fillet, is also used to further reinforce the attachment of the chamber housing (30) to the main body (20). In some preferred embodiments, the ring joint (210) abuts against the shoulder portion (36) and the opening surface of the elongated cavity (24). The ring joint (210) provides additional strength to securely hold the chamber housing (30) in the main body (20). Although not shown in the drawings, in some embodiments, an O-ring may be placed between the shoulder portion (36) of the chamber housing (30) and the opening surface of the elongated cavity (24) to provide an additional air and fluid tight seal.

It is contemplated that the chamber housing (30) is formed of glass or other suitable materials, such as plastic, ceramic, polycarbonate or the like. However, in the preferred embodiment, the chamber housing (30) is transparent so that the injection material and the various moving parts can be visually examined by the user during treatment of a subject and/or to monitor or test the function of the device.

A cap (40) may be mounted on the end of the chamber housing (30) to cover the orifice (34). The cap (40) provides and maintains sterility of the injection device (10) and prevents an accidental discharge of the injection material. Threads (41) for mounting the cap (40) are on the outer surface of the end portion of the chamber housing (30). The cap (40) has matching threads (42) on the inner surface, so that the cap (40) can be screwed-on at the end portion of the chamber housing (30). Once screwed-on, the cap (40) provides an air and fluid tight seal around the orifice to prevent any foreign material from being introduced into the device. In alternative embodiments, the cap (40) and the end portion of the chamber housing (30) can be configured so that the cap (40) is snapped-on instead of screwed-on. The cap (40) may be made of any suitable material. However, in preferred embodiments, the cap is composed of rigid material such as plastic polymers, rubber, ceramic or the like.

The piston (50) has an elongated cylindrical body (51) with an indented front surface (52) at one end and a head (54) at the opposite end. The head (54) includes a rear surface (55), which is preferably concave. In alternative embodiments, the front and rear surfaces may be flat, or have other suitable shapes. The elongated cylindrical body (51) of the piston (50) is disposed inside the liquid chamber (33) for sliding movement along its length. In preferred embodiments, the elongated cylindrical body (51) has substantially the same outer diameter as the diameter of the liquid chamber (33) to provide free sliding movement along the length of the liquid chamber (33). Due to an air and fluid tight seal around a plunger (56), the air and fluid tight seal around the piston (50) may not be necessary. In alternative embodiments, the head (54) of the piston (50) has substantially the same outer diameter as the inner diameter of the elongated cavity (24) to form an air and fluid tight seal with a minimal friction between the head (54) and the walls of the elongated cavity (24). The space defined between the head (54) and the back wall of the elongated cavity (24) is the second gas chamber (90). The head (54) is disposed inside the elongated cavity (24) so that the compressed gas introduced in the second gas chamber (90) expands the head (54) against the wall surface of elongated cavity (24), providing an additional seal, so that the compressed gas introduced into the second gas chamber (90) pushes the piston (50) forward.

In some embodiments, where the lower portion (57) of the head (54) makes contact with the neck portion (32) of the chamber housing (30), the shapes of both portions may be configured to match each other. In the preferred embodiment, the end surface (230) of the neck portion (32) forms a concave surface while the lower portion (57) of the head (54) forms a convex surface. The matching shapes assist in delivering substantially all of the injectable material in the liquid chamber (33) to the desired injection site. However, in alternative embodiments, other suitable shapes, such as a flat surface, may be used, and the piston (50) may be made of any suitable material such as plastic, glass, ceramic, metal, composites or the like.

In preferred embodiments, a plunger (56) is positioned inside the liquid chamber (33). The plunger (56) has an outer diameter which is substantially the same as the inner diameter of the liquid chamber (33) to form an air and fluid tight seal. The plunger (56) is disposed between the piston (50) and the orifice (34). The injectable material is situated in front of the plunger (56) (i.e., between the orifice (34) and the plunger (56)) so that the forward movement of the plunger (56) forces the injectable material toward the orifice (34). The front surface of the plunger (56) may be configured to match the opening defined by an orifice guide (240). In preferred embodiments, the front surface of the plunger (56) has a convex surface to match the concave shape of the orifice guide (240), whose vertex is the orifice (34). The shape of the orifice guide (240) focuses and increases the velocity of injectable material as it exits the orifice (34). The matching shapes of the orifice guide (240) and the plunger (56) tend to minimize the waste of injectable material, since most of the injectable material is forced out through the orifice (34). The shape of the rear surface of the plunger (56) matches the front surface (52) of the piston (50). The similarly shaped configuration provides for an even distribution of the pressure on the rear of the plunger (56) when the piston (50) moves forward. This tends to minimize jams or distortion as the plunger (56) is driven forward. In some embodiments, the plunger (56) is made of rubber or other suitable materials, such as plastic, composites or the like. In alternative embodiments, the plunger (56) and the piston (50) are formed as an integrated piece either by attaching the plunger (56) to the piston (50) or by molding the piston assembly to include the plunger (56).

In preferred embodiments, the device further comprises a resistance sensitive trigger which includes an actuating member (250) that is an elongated tubular member that slides over the second body portion (22) of the main body (20). The actuating member (250) has a trigger portion (251), a raised rail, and a retainer slot (253). The actuating member (250) is enclosed at one end and has an opening at the other end. On the inner surface of the enclosed end, there is a spring surface (254) for holding or mounting a coil spring (255). In some embodiments, the resistance sensitive trigger also includes a coil spring (255) that is positioned between a spring surface (254) and the chamber plug (28) and provides a resilient bias toward the rear end. As the proper use of the injection device (10) requires that the injector device (10) be positioned substantially perpendicular to the skin surface of the subject before the injectable material is injected into the injection site, the tension strength of the coil spring (255) is sufficiently strong to prevent accidental triggering when the injection device (10) is not properly positioned. Typically, a minimum applied pressure of 2.2 lbs/in.sup.$^2$ (1.0 kg/2.5 cm.sup.$^2$) is required to discharge the injector. However, slightly lower or higher minimums may be required, depending on the skin of the subject, the location at which the injection is to be administered, or the desired depth of the treatment. In alternative embodiments, alternate resistance elements may be used instead of the coil spring (255), including, but not limited to deformable rubber or plastic, strain gauges or the like.

In some embodiments, a retainer slot (253) is positioned in the front opening of the actuating member (250), for mounting a retainer (256). The retainer slot (253) is formed around the inner circumference of the actuating member (250), extending from one side of the raised rail to the other side. The retainer (256), which in preferred embodiments is in a form of a thin circular rod, is mounted into the retainer slot (253). In some embodiments, the circumferential length of the retainer (256) is substantially equal to that of the retainer slot (253). In these embodiments, when the actuating member (250) is installed onto the second body portion (22), the retainer (256) generally rests against the flange (27). This prevents the actuating member (250) from detaching itself from the second body portion (22) due to rearward force exerted by the coil spring (255). In preferred embodiments, the retainer (256) may be made of plastic or other suitable materials such as metal or the like. In alternative embodiments, the retainer (256) and the actuating member (250) may be formed as one integral member by molding process or other suitable processes. The actuating member (250) is typically made of plastic or other suitably rigid and resilient materials, such as glass, composite, ceramic or metal. In some embodiments, the trigger portion (251) is on the outer end surface of the actuating member (250). It preferably forms a concave surface and is coated with a textured material to prevent depressing force, such as from a thumb, from slipping.

In some preferred embodiments, when the actuating member (250) is not depressed, the lever (81) rests on the flat thinner inner surface of the raised rail. This is the normal state of the injection device (10) prior to injection. When the actuating member (250) is depressed, the actuating member (250) moves forward, and forces the lever (81) toward the center of the second body portion (22). The inward movement of the lever displaces the release valve (110) and consequently releases the compressed gas in the first gas chamber (70). The raised rail can be formed as an integral part of the actuating member by a molding process or other suitable processes.

In some embodiments, the second body portion (22) includes three spines (400) and the actuating member (250) includes corresponding three spline slots (401) adapted to slidably receive the spines (400) of the second body portion (22). The spines (400) and spline slots (401) are provided to assist the actuating member (250) to slide along the second body portion as the actuating member (250) is depressed to deliver an injection. The spines (400) and spline slots (401) substantially prevent the actuator member (250) from rotating about the second body portion (22) to avoid jamming of the actuating member (250) during an injection. The spines (400) and spline slots (401) also prevent rotational movement of the actuating member (250) about the second body portion (22) when the cap (40) is removed or threaded onto the chamber housing (30). This limits the amount of torsional stress placed on the lever (81) in the passageway (80) during an injection or when removing or threading the cap (40) onto the chamber housing (30). In alternative embodiments, a different number of spines and spline slots may be used. Also, if the lever (81) is sufficiently strong enough the spines and spline slots may be eliminated. In further alternatives, the spines (400) and/or spline slots (401) may be coated with a lubricant or formed from materials with low frictional coefficients to facilitate sliding movement of the actuating member (250) along the second body portion (22). In preferred embodiments, the spines (400) and spines slots (401) have a rectangular cross-section. However, in alternative embodiments, the spines and spline slots may have other cross-sections, such as triangular, saw tooth, dove tail or the like, to resist rotational movement of the actuating member (250) about the second body portion (22).

The operation of the needleless injector device according to the preferred embodiment will now be discussed. The user unscrews or unsnaps the cap (40) from the main body (20), thus revealing the orifice (34) of the injector device (10). The user then positions the injector device (10) perpendicularly against the skin surface to provide firm and secure contact of the orifice (34) against the skin surface. The injector device (10) requires the device (10) to be properly oriented and in contact with the skin of the patient, since the injector device (10) is designed so that it cannot be activated or discharged without the device (10) being placed against the skin surface. Otherwise, with the high fluid delivery velocity, a jet injector could injure a person's eye or other part of the body.

As the trigger portion (251) of the actuating member (250) is depressed, the skin surface of the patient resists the pressure being applied to the actuating member (250) of the resistance sensitive trigger and the coil spring (255) is compressed between the chamber plug (28) and the spring surface (254). Sufficient pressure (generally a minimum of 2.2 lbs/in.sup.2 [1.0 kg/2.5 cm.sup.2]) must be applied at the trigger portion (251) to overcome the tension of the coil spring (255). Concurrently, as the inclined region pushes against the lever (81), the lever (81) is pushed inward toward the center axis of the main body (20). As the actuating member (250) is pressed further against the skin surface, the lever (81) pushes against the side of the release valve (110), displacing the release valve (110). This exposes the opening of the passageway (100), and the compressed gas stored in the first gas chamber (70) is released into second gas chamber (90). When sufficient pressure is built up inside the second gas chamber (90), the piston (50) is pushed forward so that it slides forward in the liquid chamber (33). The seal around the head (54) of the piston (50) substantially prevents any gas from leaking into the other parts of the elongated cavity. The forward movement of the piston (50) causes the front surface (52) of the piston (50) to make contact with the rear surface of the plunger (56), to move the plunger (56) forward. As the plunger (56) moves forward, the injectable material exits from the orifice (34) at a high velocity and penetrates the skin surface at the injection site.

As shown in FIG. 2A–C, a needless injection device according to a second embodiment of the present invention is embodied in a pen-sized device. As shown in FIG. 2A, the needless injector device (300) comprises an outer casing (301), a disposable nozzle tip (302), a movable activator (303), a pigment well lid (304), a pigment inlet (305), and a $CO_2$ cartridge (306). The injector device (300) may also comprise a pressure regulator device to maintain the pressure within the injector device (300) upon changes in the ambient temperature. Where appropriate, the injector device (300) incorporates the design features described in detail above.

In preferred embodiments, the outer casing (301) is made of any durable material such as various plastics, metals, glasses, or ceramics. The casing can include a textured outer surface to assist in gripping or holding the device. The outer casing can also include instructions, warnings, identification marks or other desired text. The outer casing (301) is designed to be associated with other structural elements including various access panels (e.g., pigment well lid (304) and a $CO_2$ cartridge access panel). The access panels may be attached to or incorporated into the outer casing (301), for example, by hinges, snaps, hook and eye attachments, and the like or may be sliding panels. The access panels allow the technician to gain access to the interior of device through openings in the outer casing (301), for example, to replace or insert pigment ampules (309) or $CO_2$ cartridges (306).

As shown in FIGS. 2A and 2B, in some embodiments, the outer casing encloses the $CO_2$ cartridge (306), a channel (307) that allows passage of the injectable material and air flow from the $CO_2$ cartridge (306), channel guides (308), and an attachment zone for attachment to the movable channel activator (303) and the disposable nozzle tip (302).

In preferred embodiments, the movable activator (303) is attached to the outer casing either permanently (e.g., adhesively or through molding during production) or detachably (e.g., threading or any conventional fasteners to facilitate quick removal of or attachment to the injector outer casing (301)). When sufficient force is applied to movable activator through contact of the device with the skin of a subject, the activator causes movement in the channel (307), backward inside the inner cavity of the device, such that the pigment inlet (305) is in position to allow pigment to enter the channel (307) and such that the $CO_2$ cartridge is triggered to discharge. For example, the movement of the channel (307) can align the pigment inlet (305) with a pigment outlet (310) in the pigment ampule (309). A microdroplet of pigment (311) from the pigment ampule (309) enters the channel (307), for example, because of pressure release caused by access of the pigment to the channel (307). Additionally, the movement of the channel (307) displaces a valve sealing one end of the $CO_2$ cartridge (306), such that gas is discharged from the $CO_2$ cartridge (306) through the channel, forcing the microdroplet of pigment (311) to travel through the channel (307), out of the device (300), and through the skin of the subject. In preferred embodiments, the discharge also causes the channel (307) to return to its original position.

In some embodiments, the disposable nozzle tip (302) is attachable to the ejector end of the device and can be attached to either the movable activator (303) or the outer casing (301). The nozzle assembly includes external acme threading or any conventional fasteners to facilitate quick removal of or attachment to the injector. In preferred embodiments, the nozzle tip (302) is formed of a strong material capable of withstanding high pressure and stress such as gamma stabilized high impact polycarbonate, polypropylene and any derivatives thereof, or any medical grade material or composite capable of withstanding the pressure and stress subjected by the injector during use. In preferred embodiments, the nozzle comprises a nozzle channel (312) that extends through the length of the nozzle tip (302). The channel is designed to align with the channel (307) of the injection device (300). In the embodiment shown in FIG. 2B, the channel (307) extends through the movable activator (303), with the nozzle channel (312) having a diameter at the base (313) of nozzle tip (302) that allows insertion of the channel (307) into the channel (312), forming a contiguous path for the flow of the injectable material. When attached to the injection device (300), the base (313) of the disposable nozzle tip (302) is in contact with the movable activator (303), such that contact and seating of the tip (314) of the disposable nozzle tip (302) with the skin of a subject can be physically transmitted to the movable activator (303). In some embodiments of the present invention, the disposable nozzle tip (302) is made of a transparent material to allow monitoring of the flow of injectable material through the nozzle tip (302). Examples of nozzles that find use with hypodermic injectors include those described in U.S. Pat. Nos. 5,722,953, 5,697,917, and 5,643,211, herein incorporated by reference in their entireties.

In preferred embodiments, the pigment or other cosmetic material to be injected is contained in one or more ampules (309) which is contained within the outer casing (301). In preferred embodiments, the ampules can be inserted, removed, and replaced as desired. However, the present invention contemplates that the ampules may be permanently incorporated into the injection device (300) during production and that once emptied, the injection device (300) is discarded. In other embodiments, micropigments are injected into the channel from a plurality of injection tubes attached to a plurality of ampules (either inside or outside of the device), such that a microdroplet of pigment or other material is injected into the channel in a controlled manner (e.g., activation of a button or lever that controls the displacement of a release valve at the end of the injection tube contained within the injection device). Such embodiments allow multiple materials, combinations, or mixtures to be injected. As shown in FIG. 2A and 2B, the ampule comprises a pigment outlet (310). The pigment outlet (310) can be an opening in the ampule that allows passage of a small portion of the pigment contained in the ampule. Prior to placement in the injection device (300), the pigment outlet is preferably sealed, for example, by a removable adhesive strip. Just prior to placement in the device, the seal is removed. However, it is contemplated the seal may be removed during or after placement of the ampule in the injection device. For example, a projectile contained on the outer surface of the channel (307) can break the seal after the ampule (309) is inserted into injection device (300) and after the pigment well lid (304) is closed. Movement of the channel (307) following proper contact and seating of the nozzle tip (302) on the skin of a subject, aligns the pigment inlet (305) of the channel (307) with the pigment outlet (310), allowing transfer of a microdroplet of pigment from the ampule (309) to the channel (307). The material in the ampule (309) enters the channel due to a differential pressure between the inside and outside of the ampule (309). The pressure differential can be created, for example, by pressure loading and sealing the ampule (309), by applying pressure from the closure of the pigment well lid (304), or by having a moveable barrier compress the ampule (e.g., compress the ampule in conjunction with the activation of the movable barrier). It is contemplated that multiple ampules, or multichamber ampules, containing more that one type of injectable material can be incorporated into a single injection device (300).

The injection device (300) may also comprise one or more channel guides (308) within the outer casing (301), movable activator (303), or nozzle tip (302). The channel guides comprise an outer diameter that attaches to the inner surface of the outer casing (301), movable activator (303), or nozzle tip (302). The channel guides further comprise an inner diameter comprising an opening that securely encompasses the channel (307), maintaining the channel in a desired linear trajectory. The channel guides are made of a rigid and durable material that maintains the position and direction of the channel (307) while allowing the channel (307) to slide within the openings. Such materials include metals, plastics, glasses, ceramics, and the like.

In operation, the disposable nozzle tip (302) of the injector device (300) attaches to the movable activator (303) at the front of the device. The nozzle tip (302) pressed against the skin depresses the movable activator (303) which moves the channel (307) backward inside the inner cavity of the instrument. The channel (307) directs the micro-pigment droplets through the nozzle tip (302), propelled by the jet of air from the $CO_2$ cartridge (306). The channel (307) is opened at both ends. The channel contains a micro-pigment inlet (305) which, when passed across the pigment ampule (309) located above the channel (307), releases a single droplet into the channel (307). The channel (307) continues backward and triggers the $CO_2$ cartridge (306) activating a jet of air through the channel (307) carrying the micro-droplet through the channel (307) into the nozzle tip (302) and injecting it into the epidermis layer within a fraction of a second, creating a permanent deposit into the skin. The channel (307) and the moveable activator (303) return to their normal pre-depressed position. This procedure can be repeated to obtain the desired effect.

In alternate embodiments of the present invention, the energy mechanism is provided as a suitable air compressor that provides burst of compressed air upon activation by the technician. As shown in FIG. 2C, the outer casing (301) is penetrated by an air compressor inlet valve (500). The inlet valve is connect, either by construction or detachably, to a compressor channel (501), which is in gaseous communication with the channel (307). The compressor inlet valve is connected at its external end (502) to any of a variety of compressed gas sources, including, but not limited to a suitable air compressor, external pressurized gas tank, and the like. The internal end (503) of the compressor inlet valve (500), comprises an activator piston (504) with an opening on its inner end (506), in gaseous communication with the compressor channel (501). The activator piston contains an opening at its lowed end, which, in an inactive state is blocked from gaseous communication with a compressor inlet valve chamber (505). When the activator piston (504) is depressed, the opening in the activator piston (504) is lowed and exposed to the compressor inlet valve chamber (505) allowing gaseous communication between the compressor inlet valve chamber (505) and the compressor channel (501). The activator piston is depressed by contact with a trigger (507), which is exposed on one end to the outside of the outer casing (301), allowing activation by the technician. In some embodiments, the trigger (507) is prevented from being depressed unless an actuating member is activated by pressure between the end of the injection device and the surface of the skin. Thus, the injection device must be in contact with the skin and the technician must depress the trigger to initiate injection.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in appropriate fields are intended to be within the scope of the following claims.

We claim:

1. A system comprising a needleless injector suitable for injecting pigment through a skin surface of a subject, the needleless injector comprising: a pigment; a housing, wherein said housing comprises an injection end comprising an orifice; an ampule containing said pigment; a driver capable of forcing said pigment out of said orifice of said injection end of said housing at a sufficient velocity to pierce the skin surface of said subject; and an energy mechanism for moving said driver, wherein said energy mechanism comprises compressed gas, wherein said compressed gas is supplied by a suitable air compressor attached to said housing through at least one tube.

* * * * *